(12) United States Patent
Hwang

(10) Patent No.: US 9,364,628 B2
(45) Date of Patent: Jun. 14, 2016

(54) CURVATURE-ADJUSTABLE ENDOTRACHEAL TUBE

(75) Inventor: Sung Oh Hwang, Wonju-si (KR)

(73) Assignee: YONSEI UNIVERSITY WONJU INDUSTRY-ACADEMIC COOPERATION FOUNDATION (KR)

(*) Notice: Subject to any disclaimer, the term of this patent is extended or adjusted under 35 U.S.C. 154(b) by 249 days.

(21) Appl. No.: 14/113,644

(22) PCT Filed: Apr. 27, 2012

(86) PCT No.: PCT/KR2012/003305
§ 371 (c)(1),
(2), (4) Date: Oct. 24, 2013

(87) PCT Pub. No.: WO2012/148226
PCT Pub. Date: Nov. 1, 2012

(65) Prior Publication Data
US 2014/0041665 A1   Feb. 13, 2014

(30) Foreign Application Priority Data

Apr. 28, 2011   (KR) .................. 10-2011-0040260

(51) Int. Cl.
*A61M 16/00*   (2006.01)
*A61M 16/04*   (2006.01)

(52) U.S. Cl.
CPC ............ *A61M 16/0434* (2013.01); *A61M 16/04* (2013.01); *A61M 16/0418* (2014.02)

(58) Field of Classification Search
CPC ............ A61M 16/04; A61M 16/0418; A61M 16/0434; A61M 16/0409; A61M 16/0415; A61M 16/0488; A61M 2205/32; A61M 2210/0618; A61M 2230/005; A61M 25/0152; A61M 25/09025; A61M 25/09033; A61B 1/2676; C10M 2209/104
USPC ............ 128/200.26, 207.15, 207.18; 600/434
See application file for complete search history.

(56) References Cited

U.S. PATENT DOCUMENTS 2,541,402 A * 2/1951 Caine .................. A61B 1/2676
                                                  128/200.26
2,975,785 A * 3/1961 Sheldon ............. A61B 1/00165
                                                  277/634

(Continued)

FOREIGN PATENT DOCUMENTS

JP   2005510310   4/2005
JP   2006204464   8/2006

(Continued)

OTHER PUBLICATIONS

International Search Report—PCT/KR2012/003305 dated Nov. 26, 2012.

(Continued)

*Primary Examiner* — Jason Flick
*Assistant Examiner* — Victoria Leszczak
(74) *Attorney, Agent, or Firm* — Cantor Colburn LLP

(57) ABSTRACT

Provided is a curvature-adjustable endotracheal tube. The curvature-adjustable endotracheal tube includes: a hollow cylindrical tube body configured to maintain a patient's airway; and a curvature-adjusting wire configured to allow an operator to freely adjust the curvature of the tube body to correspond to the curvature of the patient's airway into which the tube body is inserted. Both ends of the curvature-adjusting wire are respectively fixed to a distal portion and a proximal portion of the tube body such that the distal portion is pulled and bent when the proximal portion is bent by the operator.

5 Claims, 3 Drawing Sheets

(56) References Cited

U.S. PATENT DOCUMENTS

| | | | | |
|---|---|---|---|---|
| 3,162,214 | A * | 12/1964 | Bazinet, Jr. | A61B 1/0055 138/120 |
| 3,773,034 | A * | 11/1973 | Burns | A61M 25/0155 600/434 |
| 3,906,938 | A * | 9/1975 | Fleischhacker | A61M 25/09033 600/585 |
| 4,150,676 | A * | 4/1979 | Jackson | A61M 16/04 128/207.15 |
| 4,215,703 | A * | 8/1980 | Willson | A61M 25/09033 600/585 |
| 4,257,421 | A * | 3/1981 | Beal | A61M 25/09 600/434 |
| 4,329,983 | A * | 5/1982 | Fletcher | A61M 16/0418 128/207.14 |
| 4,589,410 | A * | 5/1986 | Miller | A61M 16/0418 128/207.15 |
| 4,622,965 | A * | 11/1986 | Teeple | A61M 16/0418 128/204.25 |
| 4,958,642 | A * | 9/1990 | Christian | H01R 13/33 439/448 |
| 5,125,895 | A * | 6/1992 | Buchbinder | A61M 25/09041 604/95.01 |
| 5,231,989 | A * | 8/1993 | Middleman | A61B 1/00165 600/434 |
| 6,321,749 | B1 * | 11/2001 | Toti | A61M 16/04 128/200.26 |
| 6,585,717 | B1 * | 7/2003 | Wittenberger | A61M 25/0138 604/523 |
| 8,133,241 | B2 * | 3/2012 | Boyd | A61B 17/064 606/151 |
| 2002/0096177 | A1 * | 7/2002 | Toti | A61M 16/0418 128/207.15 |
| 2007/0017527 | A1 * | 1/2007 | Totz | A61M 16/04 128/207.15 |
| 2007/0028923 | A1 | 2/2007 | Souris et al. | |
| 2009/0306626 | A1 * | 12/2009 | Sinha | A61J 15/0003 604/516 |

FOREIGN PATENT DOCUMENTS

| | | |
|---|---|---|
| JP | 2011036489 | 2/2011 |
| KR | 1020030003636 | 1/2003 |
| KR | 1020040062641 | 7/2004 |
| WO | 9001964 | 3/1990 |
| WO | 03045485 | 6/2003 |

OTHER PUBLICATIONS

European Search Report—European Application No. 12777197.0 issued on Oct. 17, 2014, citing AU 2002 239 351, WO 90/01964 and US 2007/028923.

* cited by examiner

CURVATURE-ADJUSTABLE ENDOTRACHEAL TUBE

TECHNICAL FIELD

The present invention relates to a curvature-adjustable endotracheal tube, and more particularly, to a curvature-adjustable endotracheal tube in which an operator may adjust the curvature of the endotracheal tube itself according to the curvature of a patient's airway in a state where the endotracheal tube is intubated into the patient's trachea.

BACKGROUND ART

In general, an endotracheal intubation refers to an airway maintenance method which is essentially performed for a patient who suffers from respiratory failure or airway obstruction or a patient who requires aid to influence breathing such as a patient under anesthesia.

An endotracheal tube is used for such an endotracheal intubation. The endotracheal tube is intubated into the inside of the trachea mainly through the mouth (or nose) and then through the oral cavity, the pharynx, the larynx, and the glottis. Thus, the endotracheal tube is fabricated in a shape somewhat curved forwardly in consideration of the human body's structure through which the endotracheal tube passes in the process of intubation.

When performing an existing endotracheal intubation, the endotracheal tube should be bent further as compared with the curvature of the endotracheal tube formed at the time of fabricating the endotracheal tube in order to facilitate the intubation into the trachea. Thus, the intubation is typically performed in a state where the endotracheal tube is bent further by inserting a relatively rigid iron core into the endotracheal tube.

Individual patients who need endotracheal intubation have different anatomical curvature of the airway where the endotracheal tube passes through. Therefore, there is, not infrequently, a need to change the curvature angle of endotracheal tube while endotracheal intubation is being performed. However, the existing endotracheal tube is hardly bent further or unbent in the process of performing the intubation when the endotracheal tube is used in the state where the iron core is inserted into the endotracheal tube. This is because it is impossible to bend the iron core in the state where the endotracheal tube is intubated into the trachea.

Accordingly, unless the curvature maintained by the iron core is suitable for a patient, it is required to pull out the endotracheal tube again and adjust the curvature of the endotracheal tube. However, this may delay the intubation and put the patient in danger. Further, when the iron core is exposed to the outside of the endotracheal tube, the iron core may pierce the trachea, thereby causing serious damage or bleeding.

In addition, after the endotracheal intubation is completed, the iron core should be removed. In the process of removing the iron core, the endotracheal tube may be pulled out from the trachea.

DETAILED DESCRIPTION OF THE INVENTION

Technical Problem

A technical object of the present invention is to provide a curvature-adjustable endotracheal tube which may not only make endotracheal intubation easier but also prevent damage of the trachea and bleeding while the curvature of the endotracheal tube itself is adjusted according to the curvature of a patient's airway in a state where the endotracheal tube is intubated into the patient's trachea, enables repeated attempts of the endotracheal intubation, and may reduce an operation time, thereby improving the quality of the endotracheal intubation.

The technical objects to be accomplished by the present invention are not limited to the technical object as described above and other technical objects which have not been described above may be clearly understood by a person ordinarily skilled in the art to which the present invention belongs from the following description.

Means for Solving the Problems

In order to achieve the technical objects as described above, the present invention provides a curvature-adjustable endotracheal tube including: a hollow cylindrical tube body configured to maintain a patient's airway; and a curvature-adjusting wire configured to allow an operator to freely adjust the curvature of the tube body to correspond to the curvature of the patient's airway into which the tube body is inserted. Both ends of the curvature-adjusting wire are respectively fixed to a distal portion and a proximal portion of the tube body such that the distal portion is pulled and bent when the proximal portion is bent by the operator.

The curvature adjusting wire may include a first joint fixed to a side of an inner circumferential surface of the distal portion; a second joint fixed to a side of an inner circumferential surface of the proximal portion to be diametrically opposite to the fixed position of the first joint; and a connecting portion disposed slantly within a hollow portion of the tube body so as to interconnect the first joint and the second joint.

The tube body may include a first corrugated tube which is provided on a surface of the distal portion so as to allow the distal portion to be bent by being folded according to an operation of the curvature adjusting wire.

The tube body may include a second corrugated tube which is provided on a surface of the proximal portion so as to allow the proximal portion to be bent by being folded according to an operation of the curvature adjusting wire.

The endotracheal tube may further include a lever which is provided at an end of the curvature adjusting wire adjacent to the proximal portion so as to allow the operator to grip the lever by hand.

The lever may be formed in a ring shape so as to allow the operator to hook a finger into the lever to pull the curvature adjusting wire.

The distal portion may be processed such that one end of the distal portion is tapered to be easily inserted into the patient's airway.

The endotracheal tube may further include a balloon coupled to the distal portion and configured to fix the position of the tube body by being inflated after the distal portion is inserted into the patient's airway.

Effect of the Invention

The present invention provides a curvature-adjustable endotracheal tube in which the curvature of the distal portion is adjusted according to the operation of the curvature adjusting wire that is configured to be pulled toward the proximal portion provided in the tube body in line with a change of the curvature of the proximal portion. As a result, the curvature of the distal portion inserted into the airway may be freely adjusted by the operator while preventing the damage of the trachea and bleeding during the endotracheal intubation, the endotracheal intubation may be attempted repeatedly, and the operation time may be reduced, thereby making endotracheal intubation easier and improving the quality of the endotracheal intubation.

MODE FOR CARRYING OUT THE INVENTION

Hereinafter, exemplary embodiments of the present invention will be described with reference to the accompanying drawings. However, descriptions of any well-known functions or configurations may be omitted in the following description in order to clarify the gist of the present invention.

Figure 1:
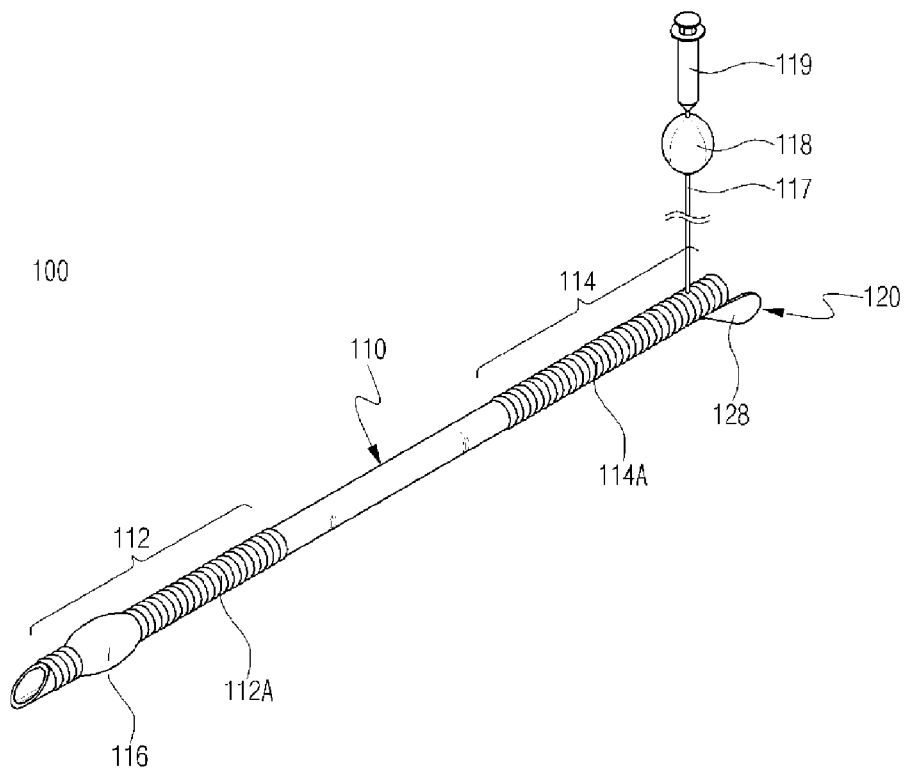
FIG. 1 is a perspective view of a curvature-adjustable endotracheal tube according to an exemplary embodiment of the present invention.
Figure 2:
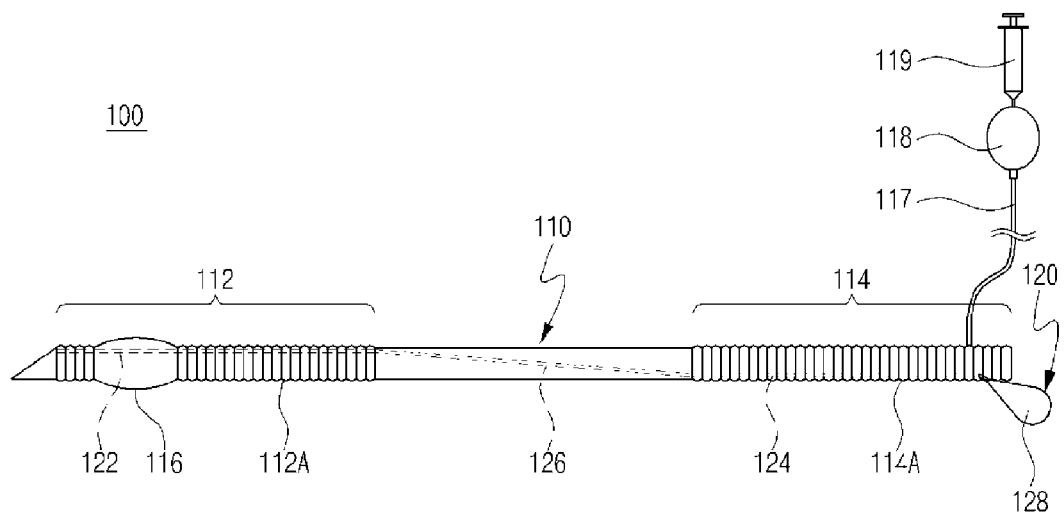
FIG. 2 is a cross-sectional view of the curvature-adjustable endotracheal tube of FIG. 1.
Figure 3:
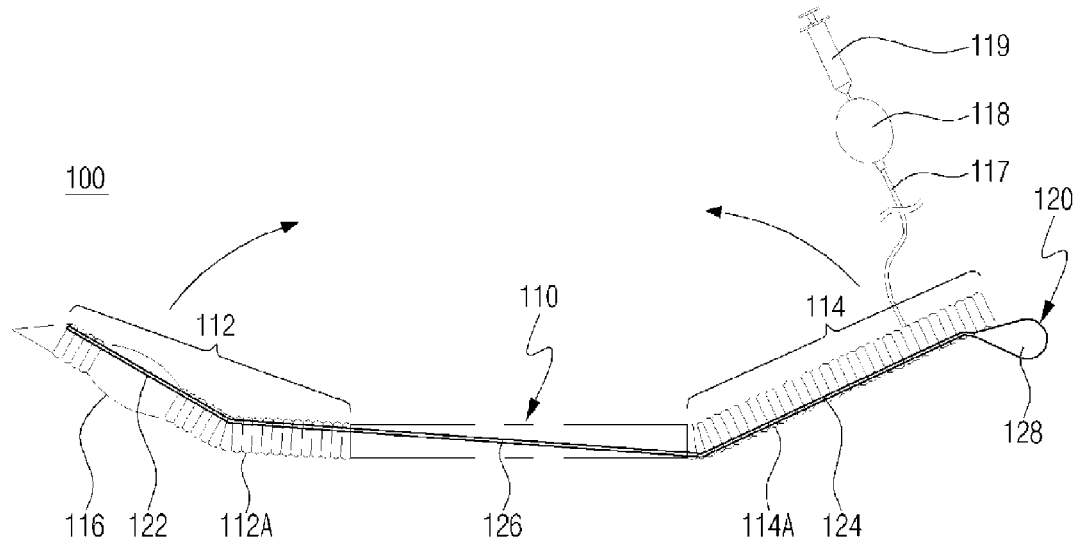
FIGS. 3 and 4 are cross-sectional views illustrating a state where the curvature of the curvature-adjustable endotracheal tube is adjusted.
Figure 4:
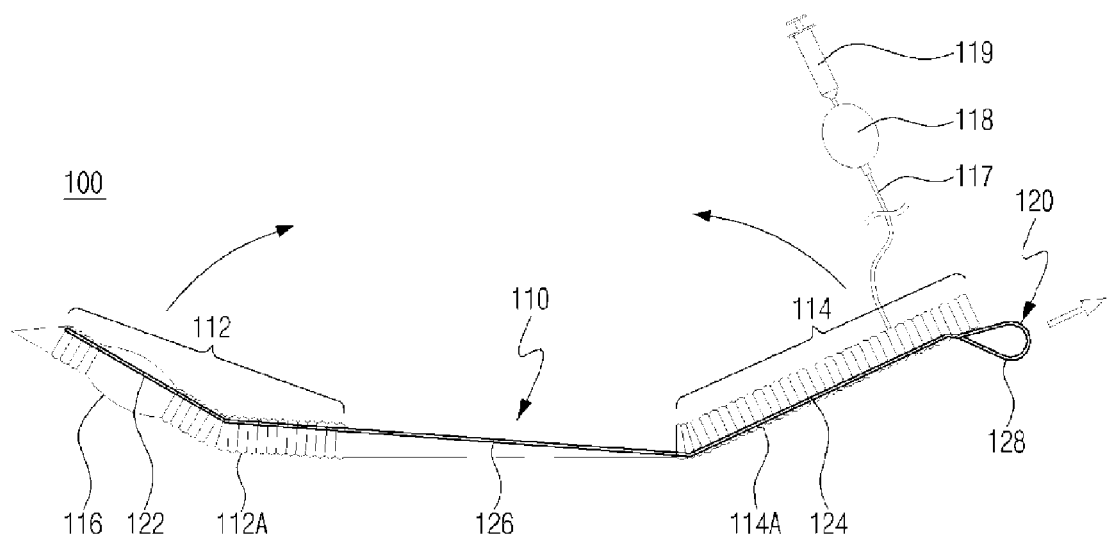
Figure 5:
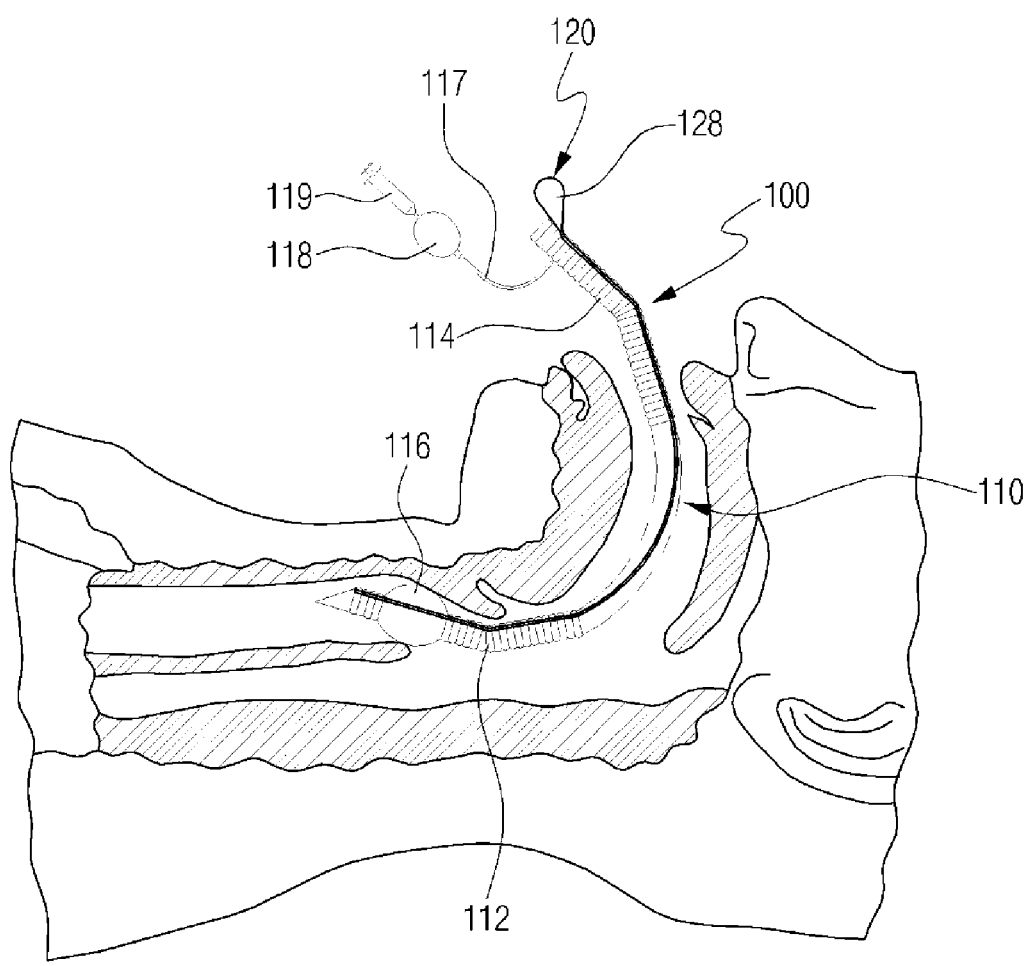
FIG. 5 is a cross-sectional view illustrating a process of performing an endotracheal intubation using the curvature-adjustable endotracheal tube of FIG. 1.

FIG. 1 is a perspective view of curvature-adjustable endotracheal tube according to an exemplary embodiment of the present invention, FIG. 2 is a cross-sectional view of the curvature-adjustable endotracheal tube of FIG. 1, and FIGS. 3 and 4 are cross-sectional views illustrating a state where the curvature of the curvature-adjustable endotracheal tube is adjusted. In addition, FIG. 5 is a cross-sectional view illustrating a process of performing an endotracheal intubation using the curvature-adjustable endotracheal tube of FIG. 1.

As illustrated in FIGS. 1 and 2, a curvature-adjustable endotracheal tube 100 according to an exemplary embodiment of the present invention includes a tube body 110 configured to supply air to a patient, and a curvature adjusting wire 120 configured to freely adjust the curvature of the tube body.

The tube body 110 is formed in a hollow cylindrical shape having a predetermined length so as to maintain a patient's airway and provided with a distal portion 112 and a proximal portion 114 at the opposite ends thereof, respectively.

The distal portion 112 is formed in a predetermined length at an end of the tube body 110 to be inserted into the patient's airway through the patient's trachea when performing an endotracheal intubation. The distal portion 112 is provided with a first corrugated tube 112A. One end of the distal portion 112 is processed to be tapered. More specifically, the end of the distal portion 112 is processed to be tapered toward the front end side. As a result, the distal portion 112 may be easily inserted into the patient's airway.

The first corrugated tube 112A is formed on the surface of the distal portion 12 such that the distal portion 112 may be bent by being folded according to the operation of the curvature adjusting wire. The first corrugated tube 112A is provided with a balloon 116. Specifically, the first corrugated tube 112A is deformed to be bent by being folded according to the operation of the curvature adjusting wire 120, thereby allowing the curvature of the distal portion 112 to be freely adjusted.

The reason why the curvature of the distal portion 112 may be adjusted when the first corrugated tube 112A is deformed to be bent by being folded according to the operation of the curvature adjusting wire 120 will be described later with reference to the curvature adjusting wire 120 to be described below.

The balloon 116 is configured to be coupled to the surface of the first corrugated tube 112A arranged at the distal portion 112 so as to fix the position of the tube body 110 after the distal portion 112 is inserted into the patient's airway. The balloon 116 is formed at the front end of the distal portion 112 inserted into the patient's airway.

The balloon 116 is connected with an air hose 117 provided along the inner circumferential surface of the tube body 110 to be exposed to the outside of the proximal portion 114 and is inflated by air introduced through the air hose 117. Accordingly, when air is introduced, the balloon 116 is inflated and comes into close contact with the inner wall of the airway. Consequently, the position of the tube body 110 may be fixed after the distal portion 112 is inserted into the airway.

Further, a check valve 118 and a syringe 119 may be removably coupled to the free end of the air hose 117 which is exposed to the outside of the proximal portion 114 so as to introduce air into the balloon 116.

The check valve 118 and the syringe 119 are coupled to the air hose 117 when introducing air into the balloon 116 and separated from the air hose 117 when pulling out the tube body 110 after the endotracheal intubation is completed. This is to discharge the air introduced into the balloon 116 through the free end of the air hose 117.

The proximal portion 114 is formed in a predetermined length at the other end of the tube body 110 so that the proximal portion 114 may be bent according to the operation of the curvature adjusting wire 120 during the endotracheal intubation. The proximal portion 114 is provided with a second corrugated tube 114A.

The second corrugated tube 114A is provided on the surface of the proximal portion 114 such that the proximal portion 114 may be bent by being folded according to the operation of the curvature adjusting wire 120. That is, the second corrugated tube 114A operates the curvature adjusting wire 120 by deforming the proximal portion 114 to be freely deformed to be bent by being folded.

The reason why the curvature of the distal portion 112 is adjusted when the proximal portion 114 is folded so that the second corrugated tube 114A operates the curvature adjusting wire 120 will be described below with reference to the curvature adjusting wire 120 to be described later.

The curvature adjusting wire 120 is configured to allow the operator to freely adjust the curvature of the tube body 110. The curvature adjusting wire 120 includes a first joint 122 fixed to the distal portion 112, a second joint 124 fixed to the proximal portion 114 to be diametrically opposite to the fixed position of the first joint 122, a connecting portion 126 configured to interconnect the first joint 122 and the second joint 124, and a lever 128 provided at the second joint 124.

The first joint 122 is configured to be fixed to a side of the inner circumferential surface of the distal portion 112. Specifically, the first joint 122 is fixed to the upper portion of the inner circumferential surface of the distal portion 112.

The second joint 124 is configured to be fixed to a side of the inner circumferential surface of the proximal portion 114. Specifically, the second joint 124 is fixed to the lower portion of the inner circumferential surface of the proximal portion 114. Accordingly, the second joint 124 is fixed to be diametrically opposite to the fixed position of the first joint 122.

The connecting portion 126 is configured to interconnect the first joint 122 and the second joint 124 and slantly disposed in the hollow portion of the tube body 110.

That is, since the first joint 122 and the second joint 124 are fixed to the distal portion 112 and the proximal portion 114 to be diametrically opposite to each other, the connecting portion 126 is disposed slantly within the hollow portion of the tube body 110 formed between the distal portion 112 and the proximal portion 114.

The lever 128 is provided at the end of the curvature adjusting wire 120 adjacent to the proximal portion 114 so that the operator may grip the lever 128 by hand. That is, the lever 128 is connected with the second joint 124 provided on the curvature adjusting wire 120 and exposed to the outside of the proximal portion 114 provided on the tube body 110 so that the operator may easily grip the lever 128 together with the proximal portion 114 when adjusting the curvature of the distal portion 112. In order to allow the operator to easily grip the lever 128, the lever 128 may be formed in a plate shape.

As illustrated in FIG. 3, the curvature adjusting wire 120 of the present exemplary embodiment is configured in such a manner that the first joint 122 is fixed to the distal portion 112 and the second joint 124 is fixed to the proximal portion 114. Thus, the curvature adjusting wire 120 is operated in line with the change of the curvature of the proximal portion 114 caused by the deformation of the proximal portion 114, thereby adjusting the curvature of the distal portion 112.

That is, when the operator deforms the second corrugated tube 114A to bend the proximal portion 114 in the state where the operator grips the proximal portion 114 and the lever 128, the curvature adjusting wire 120 operated in line with the change of the curvature of the proximal portion 114 is pulled toward the proximal portion 114. Consequently, the distal portion 112 is deformed to be bent by being folded by the first corrugated tube 112A and thus, the curvature of the distal portion 112 may be adjusted.

According to another exemplary embodiment, as illustrated in FIG. 4, the curvature adjusting wire 120 may be configured in such a manner that the first joint 122 is fixed to the distal portion 112 but the second joint 124 is not fixed to the proximal portion 114 so that, when the adjustment of the curvature of the distal portion 112 is insufficient only with the deformation of the proximal portion 114, the curvature of the distal portion 112 may be adjusted by directly pulling the curvature adjusting wire 120. In such a case, the lever 128 may be formed in a ring shape so that, when deforming the proximal portion 114, the operator may hook a finger into the lever 128 so as to pull the curvature adjusting wire 120.

That is, when the operator deforms the proximal portion 114 and at the same time, pulls the lever 128, the curvature adjusting wire 120 is pulled in the deformation direction simultaneously with the deformation of the proximal portion 114. As a result, the distal portion 112 is deformed to be bent by being folded by the second corrugated tube 112A and thus, the curvature of the distal portion 112 may be adjusted. Hereinafter, descriptions will be made on the operation procedure of the curvature-adjustable endotracheal tube according to an exemplary embodiment of the present invention with reference to FIG. 5.

As illustrated in FIG. 5, the operator grips the proximal portion 114 of the tube body 110 and the lever 128 and then inserts the distal portion 112 into the patient's trachea in order to perform an endotracheal intubation for maintaining the airway of a patient who suffers from respiratory failure or airway obstruction or a patient who requires aid to influence breathing such as a patient under anesthesia.

When the distal portion 112 of the tube body 110 is inserted into the trachea, the operator operates the curvature adjusting wire 120 by deforming the proximal portion 114 gripped by the operator by applying an external force to the proximal portion 114 so as to adjust the curvature of the distal portion 112 according to the curvature of the airway.

That is, when the proximal portion 114 is deformed to be bent by being folded by the second corrugated tube 114A, the curvature adjusting wire 120 is operated to be pulled toward the proximal portion 114 in line with the change of the curvature of the proximal portion 114. As a result, the distal portion 112, in a state in which it has been inserted in the trachea, is deformed to be bent by being folded by the first corrugated tube 112A in the direction of pulling the curvature adjusting wire 120, thereby being adjusted to maintain the curvature to correspond to the curvature of the airway.

The adjustment of the curvature of the distal portion 112 is continued until the distal portion 112 is inserted into the inside of the airway and stopped when the distal portion 112 is safely inserted into the inside of the airway.

When the distal portion 112 of the tube body 110 is inserted into the inside of the patient's airway, the patient may be stably supplied with air through the tube body 110 when a breathing disorder occurs due to, for example, respiratory failure, airway obstruction or anesthesia and thus, the patient's airway may be maintained.

As described above, the curvature-adjustable endotracheal tube 100 according to exemplary embodiments of the present invention is configured such that the curvature of the distal portion 112 is adjusted according to the operation of the curvature adjusting wire 120 configured to be pulled toward the proximal portion 114 in line with the change of the curvature of the proximal portion 114 provided at the tube body 110. Thus, when performing an endotracheal intubation, the operator may freely adjust the curvature of the distal portion 112 inserted into the airway while preventing the damage of the trachea and bleeding, repeatedly attempt the endotracheal intubation, and reduce the operation time.

In addition, since the balloon 116 inflated by air is provided on the surface of the distal portion 112 provided in the tube body 110, the balloon 116 may be inflated by introducing air after the distal portion 112 is inserted into the patient's airway so as to come into close contact with the inner wall of the airway. Therefore, when the patient's airway is secured and maintained, the position of the tube body 110 may be fixed.

The curvature-adjustable endotracheal tube 100 according to the present invention has been described as being applied to an endotracheal intubation in the above-described exemplary embodiments as an example. However, the curvature-adjustable endotracheal tube 100 is not limited thereto and may be applied to all advanced airway maintaining operations that maintain an airway using a tube.

Although specific exemplary embodiments of the present invention have been described above and illustrated, it is evident to a person ordinarily skilled in the art that the present invention is not limited to the exemplary embodiments and may be variously modified and changed without departing from the technical idea and scope of the present invention. Accordingly, such modifications and variations shall not be grasped individually and shall be considered to belong to the scope of the present invention defined by the claims.

The invention claimed is:
1. A curvature-adjustable endotracheal tube comprising:
a hollow cylindrical tube body configured to be inserted into a patient's airway, wherein the tube body comprises: a proximal portion at one end thereof; and a distal portion at the other end thereof;
a first corrugated tube disposed on an outer surface of the distal portion so as to allow the distal portion to be bent by bending of the first corrugated tube;

a second corrugated tube disposed on an outer surface of the proximal portion so as to allow the proximal portion to be bent by bending of the second corrugated tube; and a curvature-adjusting wire configured to allow an operator to freely adjust a curvature of the tube body to correspond to a curvature of the patient's airway into which the tube body is inserted, wherein the curvature adjusting wire comprises: a first joint fixed to a first side of an inner circumferential surface of the distal portion; a second joint fixed to a second side of an inner circumferential surface of the proximal end; and a connecting portion between the first joint and the second joint, the second side being diametrically opposite to the first side so that the connection portion is disposed slantly within a hollow portion of the tube body, wherein, when the proximal portion is bent by the operator, the distal portion is pulled and bent.

2. The curvature-adjustable endotracheal tube of claim 1, further comprising:

a lever which is provided at an end of the curvature adjusting wire adjacent to the proximal portion so as to allow the operator to grip the lever by hand.

3. The curvature-adjustable endotracheal tube of claim 2, wherein the lever is formed in a ring shape so as to allow the operator to hook a finger into the lever to pull the curvature adjusting wire.

4. The curvature-adjustable endotracheal tube of claim 1, wherein one end of the distal portion is tapered to be easily inserted into the patient's airway.

5. The curvature-adjustable endotracheal tube of claim 1, further comprising a balloon coupled to the distal portion and configured to fix a position of the tube body by being inflated after the distal portion is inserted into the patient's airway.

\* \* \* \* \*